(12) United States Patent
Naylor

(10) Patent No.: US 10,591,302 B2
(45) Date of Patent: *Mar. 17, 2020

(54) SELECTING ROUTES

(71) Applicant: PROJECT X LTD., London (GB)

(72) Inventor: David Naylor, London (GB)

(73) Assignee: PROJECT X LTD., London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/030,753

(22) Filed: Jul. 9, 2018

(65) Prior Publication Data

US 2019/0017829 A1 Jan. 17, 2019

Related U.S. Application Data

(63) Continuation of application No. 15/024,343, filed as application No. PCT/GB2014/052908 on Sep. 25, 2014, now Pat. No. 10,018,471.

(30) Foreign Application Priority Data

Sep. 25, 2013 (GB) .................... 1317033.7

(51) Int. Cl.
*G01C 21/20* (2006.01)
*G06F 19/00* (2018.01)
(Continued)

(52) U.S. Cl.
CPC .......... *G01C 21/20* (2013.01); *A63B 24/0062* (2013.01); *A63B 24/0075* (2013.01);
(Continued)

(58) Field of Classification Search
CPC . G01C 21/20; A63B 24/0075; A63B 24/0062; G06F 19/3481; G06F 19/00; G16H 20/30
(Continued)

(56) References Cited

U.S. PATENT DOCUMENTS

| 7,162,392 B2 * | 1/2007 | Vock | A42B 3/046 342/357.57 |
| 7,901,292 B1 * | 3/2011 | Uhlir | A63F 13/216 463/39 |

(Continued)

FOREIGN PATENT DOCUMENTS

| EP | 2 172 249 A2 | 2/2009 |
| WO | 2013/075072 A2 | 5/2013 |

OTHER PUBLICATIONS

International Search Report issued in International Application No. PCT/GB2014/052908 dated Apr. 8, 2015, 6 pages.
(Continued)

*Primary Examiner* — Jaime Figueroa
(74) *Attorney, Agent, or Firm* — Mauriel Kapouytian Woods LLP; Michael Mauriel; Lana Akopyan

(57) ABSTRACT

A method of providing route information to a plurality of users by means of a data processing device is disclosed. In one embodiment, the method comprises: receiving a first location and a second location; analysing mapping services and/or geographical or other databases or information and thereby determining a pair of routes, each route comprising a start point, an end point and a defined path from the start point to the end point, the step of analysing comprising determining the routes such that (a) a first one of the routes is in the vicinity of the first location and a second one of the routes is in the vicinity of the second location and (b) the routes are of comparable difficulty for the users to complete; and providing the first route to a first one of the users and providing the second route to a second one of the users. These and other embodiments are disclosed herein.

35 Claims, 3 Drawing Sheets

(51) Int. Cl.
*G16H 20/30* (2018.01)
*A63B 24/00* (2006.01)

(52) U.S. Cl.
CPC .......... *G06F 19/00* (2013.01); *G06F 19/3481* (2013.01); *G16H 20/30* (2018.01)

(58) Field of Classification Search
USPC ...................................................... 701/1, 410
See application file for complete search history.

(56) References Cited

U.S. PATENT DOCUMENTS

| | | | | |
|---|---|---|---|---|
| 7,931,562 | B2* | 4/2011 | Ellis | A61B 5/1038 482/8 |
| 8,718,927 | B2* | 5/2014 | Kitchel | G01C 21/32 701/412 |
| 9,409,052 | B2* | 8/2016 | Werner | A63B 24/0021 |
| 10,018,471 | B2 | 7/2018 | Naylor | |
| 2005/0250458 | A1* | 11/2005 | Graham | G06Q 30/02 455/121 |
| 2008/0059064 | A1* | 3/2008 | Werner | A63B 24/0062 455/456.3 |
| 2010/0042427 | A1* | 2/2010 | Graham | G06Q 30/02 705/15 |
| 2010/0088023 | A1* | 4/2010 | Werner | A63B 24/0021 701/467 |
| 2010/0222179 | A1 | 9/2010 | Temple et al. | |
| 2010/0292600 | A1* | 11/2010 | DiBenedetto | A63B 24/0062 600/520 |
| 2011/0003665 | A1* | 1/2011 | Burton | G04F 10/00 482/9 |
| 2011/0183645 | A1* | 7/2011 | Chawla | H04M 3/42357 455/410 |
| 2012/0095578 | A1* | 4/2012 | Tchao | G06F 19/3418 700/91 |
| 2013/0166049 | A1* | 6/2013 | Werner | G06F 19/3481 700/91 |
| 2013/0210580 | A1 | 8/2013 | Watterson et al. | |
| 2013/0238235 | A1* | 9/2013 | Kitchel | G01C 21/32 701/412 |
| 2014/0303892 | A1* | 10/2014 | Morlock | G01C 21/20 701/533 |
| 2015/0081210 | A1* | 3/2015 | Yeh | G06F 16/60 701/428 |

OTHER PUBLICATIONS

Office Action issued in United Kingdom Patent Application No. GB1605283.9 dated Nov. 13, 2019, 4 pages.

* cited by examiner

SELECTING ROUTES

CROSS REFERENCE TO RELATED APPLICATIONS

This application is a continuation of Ser. No. 15/024,343 filed Mar. 23, 2016, which is a 371 application of PCT/GB2014/052908 filed Sep. 25, 2014, which claims priority to UK 1317033.7 filed Sep. 25, 2013. The entire contents of these applications are hereby incorporated herein by reference.

BACKGROUND

This invention generally relates to determining geographical routes and, in particular, routes for sporting activity. Some aspects of the invention permit routes to be normalized for the purpose of facilitating competition or comparison between geographically separated users.

Many people have difficulty in finding the motivation to maintain a regular exercise program. Some people find it particularly difficult to maintain an exercise regimen that involves continuously repetitive motions, such as running, walking and cycling.

Competition with other people and other social or community-oriented activities (such as participating together in sports training activities) can provide motivation to some people to help maintain a regular exercise program. Some people, for example, will be more motivated to exercise when competing against one or more partners than by exercising alone, and by engaging in group athletic activities. These people might benefit from exercising with partners, entering into athletic contests such as races, comparing their current performance ability with that of their friends, and engaging in group exercise activities.

Sometimes, someone in a particular geographic location would like to train or compete with other people in other geographic locations with similar interests. However, this is difficult due to the geographic separation, differences in local topography, terrain and climate, and differences in time zones, which may additionally make it impractical to compete simultaneously with others. There is therefore a need to enable people to participate and/or compete in a sporting activity when they are in different geographical locations, and potentially at different times.

SUMMARY

According to one aspect of the present invention there is provided a method of providing route information to a plurality of users by means of a data processing device, the method comprising: receiving a first location and a second location; analysing one or more databases selected from the group comprising mapping services, geographic databases and other databases and thereby determining a pair of routes, each route comprising a start point, an end point and a defined path from the start point to the end point, the step of analysing comprising determining the routes such that (a) a first one of the routes is in the vicinity of the first location and a second one of the routes is in the vicinity of the second location and (b) the routes are of comparable difficulty for the users to complete; and providing the first route to a first one of the users and providing the second route to a second one of the users.

The step of determining that the routes are of comparable difficulty may be performed in dependence on the height gains over the routes, the height gains over the routes being different. The step of determining that the routes are of comparable difficulty may be performed in dependence on the lengths of the routes, the lengths of the routes being different. The step of determining that the routes are of comparable difficulty may be performed in dependence on the terrains of the routes, the terrains of the routes being different.

The step of analysing may comprise estimating the physical difficulty of each route and determining that the estimated physical difficulty of the routes are within a predetermined threshold of each other.

The physical difficulty of a route may be represented as an estimated time to complete that route, or by a measure of the effort required to complete that route. The activity denoted by a user "completing" a route may involve that user travelling along that route. The method may comprise specifying a manner of travelling along that route and the activity denoted by each user "completing" a respective route may involve that user travelling along that route by the same specified manner.

The step of analysing may comprise estimating the physical difficulty of each route, for example the physical difficulty of a reference user or a respective user travelling along that route, optionally in the specified manner, and estimating based on data defining one or more personal characteristics of the users that the first one of the users will take a time to complete the first route that is within a predetermined threshold of a time that the second one of the users will take to complete the second route.

The personal characteristic(s) may comprise one or more of sex, weight, resting pulse, home altitude and age.

The step of determining that the routes are of comparable difficulty for the users to complete may comprise estimating the physical difficulty of each route by summing weighted estimates of one or more characteristics of that route.

The characteristics of the route may comprise one or more of distance, ascent, altitude and a value representing terrain. The characteristics of a route may additionally comprise one or more activities unrelated to the effort involved simply in travelling along the route: for example one or more static exercises.

The step of determining that the routes are of comparable difficulty for the users to complete may comprise estimating the physical difficulty of each route by means of data gathered from them and/or other users who have previously completed the routes or parts of them.

The step of determining that the routes are of comparable difficulty for the users to complete may comprise estimating the physical difficulty of each route by averaging one or more performance metrics gathered from other users in completing the routes or parts of them.

The performance metrics may include one or more of: average time among a group of other users to complete the route or part of it, average speed among a group of other users in completing the route or part of it, average cadence among a group of other users in completing the route or part of it, and average effort among a group of other users in completing the route or part of it.

The step of analysing may comprise determining the routes to be comparable by the steps of: determining a first candidate route; determining a second candidate route; comparing the candidate routes and if they are not the same or within acceptable levels of similarity; subsequently determining a sub-part of one of the first and second candidate routes that is comparable to the other of the first and second candidate routes; and selecting the sub-part of one of the first and second candidate routes as the first route and selecting the other of the first and second candidate routes as the second route. An acceptable level of similarity may be a level of similarity that is within a predetermined threshold. Similarity may be determined by reference to the time respective users are expected to spend completing respective routes and/or by reference to the effort respective users are expected to expend completing respective routes.

The effort expended by a user in completing a route may be estimated by means of a measure of the amount of energy expected to be expended by the user (taking into account known physical characteristics of that user) or a reference user in completing the route. The effort expended by a user in completing a route may be estimated by means of a measure of the amount of physical stress expected to be experienced by the user (taking into account known physical characteristics of that user) or a reference user in completing the route in a predetermined time.

The step of analysing may comprise determining the routes to be comparable by the steps of: determining a first candidate route; determining a second candidate route; comparing the candidate routes and if they are not the same or within an acceptable level of similarity; subsequently modifying either or both of the first and second candidate routes so that they are the same or within an acceptable level of similarity; and selecting the candidate routes after appropriate modification to either or both of them.

The step of analysing may comprise determining the routes to be comparable by the steps of: determining a first candidate route; determining a second candidate route; comparing the candidate routes and if they are not the same or within an acceptable level of similarity; subsequently modifying either or both of the first and second candidate routes so that they are the same or within an acceptable level of similarity; and selecting the candidate routes after appropriate modification to either or both of them; wherein the step of modifying may involve processes aimed not simply at identifying comparable routes in terms of difficulty but comparable routes optimised for greatest convenience, safety or other benefits for or goals specified by users.

The method may comprise the steps of: the first user completing the first route; and the second user completing the second route. During the said steps of completing the routes the first user and the second user may travel on at least parts of their respective routes simultaneously. During the said steps of completing the routes the first user and the second user may start travelling on their respective routes simultaneously. The first user may complete the first route before the second user starts travelling on the second route.

According to a second aspect of the present invention there is provided a method of providing performance information to a first user, the method comprising: estimating by means of a transceiver device local to the first user the location of the first user at a series of times; transmitting from the transceiver device to a data processing device remote from the first user location data representing the estimated location of the first user at a series of times; estimating at the data processing device, in dependence on the location data, the effort expended by the first user; comparing the estimated effort expended by the first user with the effort expended by a second user and thereby forming result data representing the result of that comparison; transmitting the result data from the data processing device to the transceiver device; and presenting the result data to the first user by means of the transceiver device local to the first user.

The method may comprise estimating by means of a second transceiver device local to a second user the location of the second user at a series of times; transmitting from the second transceiver device to the data processing device second location data representing the estimated location of the second user at a series of times; estimating at the data processing device, in dependence on the second location data, the effort expended by the second user; and wherein the step of comparing comprises comparing the estimated effort expended by the first user with the estimated effort expended by the second user.

The step of comparing may comprise comparing the estimated effort expended by the first user with pre-stored data representing the estimated effort expended by the second user.

The estimate of the effort expended by the first user may be dependent on any one or more of: the distance travelled by the first user as indicated by the location data, the time taken by the first user to traverse that distance, the altitude, relief and terrain of the route indicated by the location data and information regarding the route indicated by the location data as stored in mapping services and/or geographical or other databases or information accessible to the data processing device. The effort expended by a user in completing a route may be estimated by means of a measure of the amount of energy expected to be expended by the user (taking into account known physical or other characteristics of that user) or a reference user in completing the route. The effort expended by a user in completing a route may be estimated by means of a measure of the amount of physical stress expected to be experienced by the user (taking into account known physical or other characteristics of that user) or a reference user in completing the route in a predetermined time.

The method may comprise the steps of: determining by means of a data processing system a first area proximal to a first user and a second area proximal to a second user, the first and second areas being determined in dependence on a geographical database as being suitable for the performance of a pre-determined activity; transmitting an indication of the first area to the device local to the first user; and transmitting an indication of the second area to the device local to the second user.

The first location data may represent locations within the first area. The second location data may represent locations within the second area.

According to a third aspect of the present invention there is provided a data processing system for providing route information to a plurality of users, the system comprising: a communications interface configured to receive a first location and a second location; and a processor configured to analyse a geographic database and thereby determine a pair of routes, each route comprising a start point, an end point and a defined path from the start point to the end point, the analysis comprising determining the routes such that (a) a first one of the routes is in the vicinity of the first location and a second one of the routes is in the vicinity of the second location and (b) the routes are of comparable difficulty for the users to complete; and provide the first route to a first one of the users and provide the second route to a second one of the users.

According to a fourth aspect of the present invention there is provided a data processing system for providing performance information to a first user, the system comprising: a portable transceiver device configured to estimate the location of a first user at a series of times and transmit to a data processing device remote from the first user location data representing the estimated location of the first user at a series of times; and a data processing device configured to estimate, in dependence on the location data, the effort expended by the first user; compare the estimated effort expended by the first user with the effort expended by a second user and thereby form result data representing the result of that comparison; and transmit the result data from the data processing device to the transceiver device.

According to a fifth aspect of the present invention there is provided a method for analysing user activity, the method comprising: gathering by means of a first datalogger carried by a first user first motion data indicating the motion of the first user along a first course; gathering by means of a second datalogger carried by a second user second motion data indicating the motion of the second user along a second course geographically remote from the first course; and determining by means of the first motion data and the second motion data a first portion of the first course and a second portion of the second course that involve comparable effort to complete; wherein the method comprises estimating the difficulty of a part of the first portion by means of first the motion data, and the determining step comprises determining the effort of completing the first portion in dependence on the said difficulty.

The first datalogger may comprise an accelerometer and/or a gyroscope. The first motion data may comprise acceleration data derived from the accelerometer indicating the instantaneous acceleration of the datalogger and/or orientation information derived from the gyroscope indicating the orientation or angular velocity of the datalogger. The step of estimating the difficulty may be performed in dependence on the acceleration data and/or the data derived from the gyroscope. For example, the said difficulty may be estimated such that increased variability of the acceleration data and/or the data derived from the gyroscope during motion of the datalogger over the part of the first portion is determined to represent increased impedance. The said difficulty may be estimated by applying a function whereby a greater difficulty is attributed to the difficulty of a part of a route the greater the variability of the acceleration data measured over that part. The difficulty may be estimated independently of any altitude gain or loss over that part of the route. The altitude gain or loss may be estimated by means of data derived from a satellite positioning system and/or barometer located in the first datalogger.

According to a fifth aspect of the present invention there is provided a computer readable storage medium having encoded thereon non-transitory computer readable program code for implementing a method as set out above.

BRIEF DESCRIPTION OF THE DRAWINGS

The present invention will now be described by way of example with reference to the accompanying drawings. In the drawings.

DETAILED DESCRIPTION OF THE INVENTION

This disclosure below is presented in the context of a physical activity such as cycling. The disclosure can apply to any activity which requires completing a route, such as running, cycling, hiking, driving, kayaking, sailing and skiing and multi-sports activities such as triathlon.

As mentioned above, competitors or users in different geographical locations may wish to compete against each other in an activity, such as a cycle race. However, as the users are in different locations, the race conditions for each user may differ. For example, although two racing routes may cover the same distance, they may differ in terms of difficulty due to, for example, the terrain along each route. Thus, the race may not be fair because one user may have an easier or more difficult route to complete than the other user.

Figure 1A:
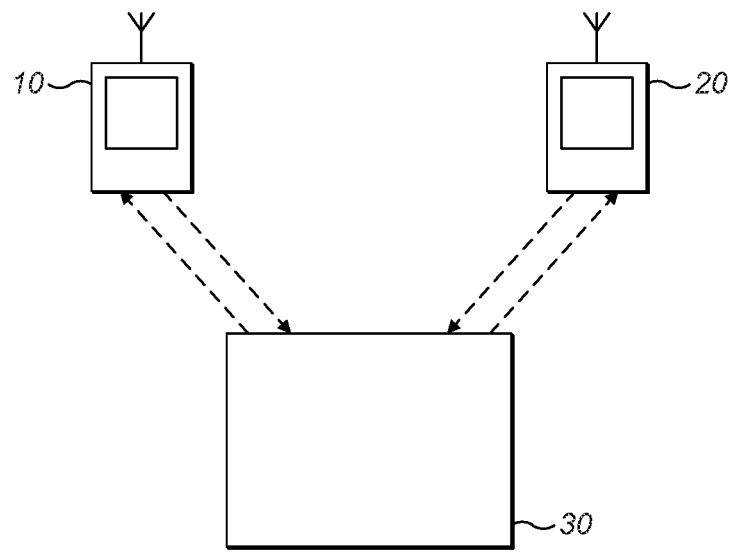
FIG. 1a illustrates a system for determining routes.
Figure 1B:
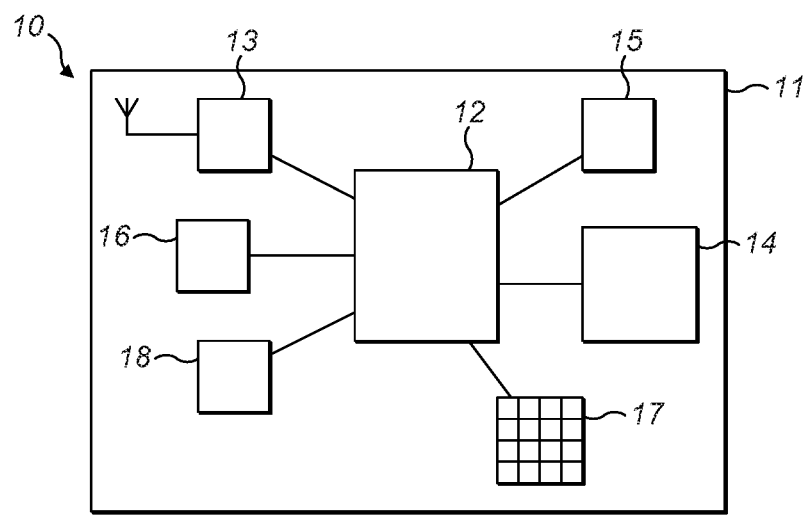
FIG. 1b illustrates a datalogger device that can be carried by a user.

FIG. 1a illustrates a system that can offer route information to users in different geographical locations. The system can help users determine routes that are comparable in terms of their physical difficulty or the physical exertion required to complete the routes. Preferably the system determines two or more routes such that if the same hypothetical person completed each route by whatever means is to be adopted by the users (running, cycling etc.) that person would be expected to take the same or substantially the same time for each route. In that way the routes are comparable.

In this example the system is provided by first and second portable devices 10, 20, which are operated by first and second users respectively, and a server 30. The server 30 may be located remotely from devices 10 and 20. The server 30 may communicate with the devices 10 and 20 over a network such as the internet. The portable devices could be handheld computers, smartphones, tablets or other computing devices. The invention could be implemented using devices whose locations are mobile or fixed. Multiple users of the system could share a single device. In the example to be described below, comparable locations or routes are computed by the server 30, but these could be computed by one of the devices 10, 20 and the server 30 could be used simply for messaging purposes or could be omitted if the devices can intercommunicate without the server.

FIG. 1a shows device 10 in more detail. Device 20 may be the same. The device comprises a housing 11 which includes a processor 12, a wireless communications interface 13, a display 14, a memory 15, a satellite positioning receiver 16, a keypad (which could be integrated into a touchscreen) or other user interface 17 and a motion sensor 18 such as an accelerometer or gyroscope. The processor 12 executes program code stored in a non-transitory way in the memory 15. The processor receives inputs from interface 13 indicating data received from a remote device such as server 30 or device 20, from the positioning receiver 16 indicating the position of the device, from keypad or other user interface 17 indicating user inputs, and from the motion sensor 18 indicating motion in the device's own frame of reference. The processor provides outputs to the communications interface to transmit data to remote devices, and to display 14 to indicate information to a user.

The first step is to initiate the computation of comparable routes for the purposes of a training session or race amongst the users. This may be accomplished in numerous ways. In one example the first user may decide that he would like to compete in a competitive activity such as a race. The first user then sends, via device 10, a request or invitation for the competitive activity to the second user. The request may be sent directly from device 10 to device 20, or via the server 30. The request could be directed to other devices or users in general and not to device 20 or its user specifically. The second user may respond to the invitation by transmitting an appropriate message from device 20 to the server or directly to device 10. If such a message indicates that the second user accepts the invitation then that initiates the process of computing comparable routes for the users. One of more of the users may specify one or more parameters (e.g. distance, duration, top speed and/or difficulty) for the race in the invitation or the response to the invitation. In another example each user could independently schedule a race or other competition at the same time in personal diaries kept on or accessible by server 30 and on identifying that the users wanted to compete at the same time the server 30 could automatically offer them both a race against each other at that time.

Once the process of computing comparable locations or routes has been initiated, one or more of the devices 10, 20 and the server 30 execute(s) a program to determine a first location or route for the first user and a second, different, location or route for the second user. That process will be described in more detail below. The distribution of the processing burden may at least partly depend on the computational capabilities of the different processing entities, and on the communication capabilities between the different entities and/or available communications networks and may be shifted between devices 10, 20 and server 30. Preferably, the majority of the processing is performed by the server 30. This is the embodiment described below. However, functions described below as being performed by the server could be performed by either device, or elsewhere.

The server 30 has access to one or more mapping services and/or geographical or other databases which hold location and mapping information and/or other information on physical areas and features such as roads, tracks, trails, lakes and rivers that may make suitable pathways for the users to follow or offer suitable locations in which users may participate in a race or other competitive activity; and/or records of routes or pathways already covered by users. The server uses these services and databases together, optionally, with other information as described below in order to compute the comparable locations or routes. The server 30 searches these services and/or databases and analyses the information available through them to identify locations or routes that are comparable and that meet any criteria specified by one or more of the users. Among the criteria that a user may specify are:

1. Approximate location where that user is to participate in the race or other activity. That location information could be determined by the user's device 10, 20 making an estimate of its position, for example by means of a GPS (global positioning system) receiver on the device or by a user of the respective device selecting or entering a location. The location may be selected or entered as an address, coordinates, a landmark, etc. or by clicking or dropping a pin on a map displayed by the user's device. The location information can indicate the position of the respective one of the devices 10, 20 or a location that is chosen by one of the users (e.g. a desired start point remote from one or more of the devices). A user or his device may also specify a zone around an indicated location in which the user is willing to participate in the race. For example, the location information could be "Washington Park, Richmond, Va." or "Latitude 54.000°, longitude −0.500°, radius 2 km".

2. The means to be adopted for the race or other activity. One or more of the users could specify that they are willing only to participate in certain types of race or other activity: for example, sailing, running or cycling.

3. Maximum or minimum length or time duration for the race or other competitive activity.

Given first location data for the first user and second location data for the second user the server 30 can process that first and second location data and any additional parameters that have been supplied and thereby determine a first route for the first user in the vicinity of the location specified by the first location data and a second route for the second user in the vicinity of the location specified by the second location data. Those routes can be determined such that they are comparable using the method described below or in other ways. Alternatively, the server 30 can use the first and second user location data and any additional parameters that have been supplied, and determine first and second comparable locations (rather than specific routes) such as a lake, park or other area defined by physical features or other boundaries, such as agreed course boundaries, in which the users can participate in a race or other competitive activity.

In one example, the server can use available mapping services and geographical or other databases to identify two pathways that are suitable for the means to be adopted for the race or other activity, a first one of the pathways being in the vicinity of the first location and a second one of the pathways being in the vicinity of the second location. It may do this by making spiral or other scans in the mapping services or databases that radiate outwards from each of the specified locations until it finds a suitable pathway that meets any criteria specified for the race or other activity. Alternatively the server can analyse the database to determine pathways within a given area defined around the first and second locations. That area around each location may be an area that is defined by a predefined or selected radius about the location or by a pair of maximum orthogonal offsets from the location. The size of the area may be dependent on the various factors such as the chosen physical activity. For example, the geographic area analysed for the activity of cycling may be larger than the area analysed for the activity of running. The geographic area analysed may increase with an expected average speed that is stored by the server for each activity.

Once candidate pathways or locations for the selected competitive activity have been identified in the vicinity of the first and second locations the user devices 10, 20 or server 30 make(s) an estimate of the level of effort that would be required and/or the time that would be taken by a hypothetical standard user to complete each pathway or complete a course within the location using the means to be adopted for the race or other activity. If those estimates are the same (or are within a preset threshold of each other, for example within 10 or 20 seconds of each other) then those locations or pathways can be offered to the users as locations or routes for a race or other activity. If the estimate for one of the locations or pathways is less than that for the other location or pathway then the user devices 10, 20 or server 30 could, in the case of pathways, determine a sub-part of the pathway whose estimate was longer such that the estimate of the time that would be taken by a hypothetical standard user to complete that sub-part is equal to (or within the preset threshold of) the estimate for the other pathway. Then the sub-part and the other pathway can be offered to the users as routes for the race. Alternatively, the shorter pathway could be extended such that the estimate of the effort required and/or time that would be taken by a hypothetical standard user to complete the extended pathway is equal to (or within the preset threshold of) the estimate for the longer pathway. Pathways could be adjusted to achieve comparability not just by lengthening or shortening them, but also by adjusting them to incorporate other features or conditions, such as greater or lesser elevation, more or less difficult terrain, and so on. The amount a route is adjusted may depend on one or more of the user's chosen race parameters. Further, either or both routes could be adjusted (within each user's chosen parameters) to deliver the 'best' available route(s) based on pre-defined criteria. Those criteria could define characteristics of routes that are generally seen as being convenient: for example favouring a reduced distance between the start and finish of the route, and reducing the number of road intersections on the route. If more than two users are to take part then this procedure can be expanded by determining sub-parts (or extensions) of each initially determined pathway until suitably optimised comparable routes have been identified. The estimates and the threshold, if any, could be expressed not only in units of time: for example they could be of the physical difficulty that would be suffered by a hypothetical standard user to complete the respective pathway or sub-part. In some cases, where adjustments to a pathway would result in a route being proposed that would not be practical or suitable for a user, the pathway may be rejected and a new one identified and the above process re-iterated, until two practical and suitable routes can be proposed. In situations where users have selected to race or participate in another activity within a specified location, such as in a park or on a lake, rather than on specific routes, if the estimate for completing the selected activity in one of the areas is less than or sufficiently different from the other, the server could select a different area or areas for either or both users or, depending on the nature of the activity selected by the users, specify different parameters for the agreed activity for one or both of the users—for example, the server could lengthen the required distance between specified points within the area around which the user must navigate to complete a lap or race. In any event, users may be able to reject a route or location, in which case another, suitable, route or location other than the rejected route could be proposed, using the approach described above.

One way to estimate the effort required and/or time that would be taken by a hypothetical standard user to complete a route is to use topographic information on the route held by or capable of being accessed from the geographical database(s). The topographic information could include variables such as relief (e.g. hilly, flat or more generally the total amount of ascent and/or descent on the route), gradient of ascents or descents along the route, changes in elevation along the route, surface(s) (smooth road, dirt path, grass, etc.), absolute altitude of points along the route, number of bends, sharpness of bends. As an illustration, a representation of time or difficulty for one activity could be estimated by the following formula:

$$(5 \times [\text{Distance in km}] + 0.03 \times [\text{Ascent in m}]) \times \begin{cases} 1, \text{terrain is road} \\ 1.2, \text{terrain is trail} \\ 1.5, \text{terrain is sand} \end{cases}$$

Other formulae could be used. Other non-topographic information to which user devices or the server has access could be incorporated into the formula. That information could include expected meteorological conditions, gravity at the user's location (which could be in space), and expected traffic conditions. Further, the formula could be applied once in respect of each location or route to determine comparable locations or routes (for example, where only variables such as total distance, total ascent, total number of bends for each location or route are already held in the database(s) or can be determined from analysing the relevant location or route), or progressively along the route and so multiple times (although this effectively could be practically simultaneous, given the processing power of modern computing devices), to generate a more sophisticated analysis of the difficulty of respective routes. In addition, the information could be comprised entirely of, or be supplemented by, information that is measured in real-time during the race or training session. This information can be used to determine if the initial difficulty calculation has changed (or has changed above a preset threshold, which could be a maximum percentage increase or decrease from the originally calculated difficulty), and if so, the route of one or both users can be adjusted accordingly. The real-time measurements may be taken periodically (e.g. every 30 seconds) and/or after a certain distance has been travelled (e.g. every 50 meters)

Another way to estimate the time and or difficulty of the pathways and sub-parts is to use a database of historic performance and other information. Many people nowadays log their physical activity (such as a run or cycle ride) using a GPS device (such as a smartphone or watch) and then upload that and other data (such as the start and end times of the activity) to an online service provider. This data can be used to determine popular routes for those activities and also the average amount of time taken by a corpus of users to complete those routes. For a popular route such a database will provide information on the times taken by many users to complete that route. The average time taken by a corpus of users to complete a route can give an indication of the physical difficulty of completing that route. When such a dataset is being used, a first route that has been completed by a set of the users in a certain average time can be considered as having a comparable or equivalent physical difficulty as a second route elsewhere that has been completed in the same time by a set of the users. Historic data from multiple users can also provide other metrics on the basis of which comparable routes can be determined, for example average speed, average heart rate, average cadence, average step count, average skin conductance and average calories burned. The data from which such indicators can be determined can be measured, logged and uploaded to the database using appropriate location-aware and/or physiologically-aware devices or applications of multiple users to provide data that can be used to estimate the difficulty in completing a route, and hence enable determinations of comparability between routes.

The algorithm used to estimate the amount of effort or energy expended in traversing all or part of a route may involve a dependency on the nature of the terrain over which that route or part-route extends. To implement such an algorithm the system may employ any one or more of a number of mechanisms. First, the system may interrogate a geographical database which holds information on the nature of the relevant terrain, and retrieve the nature of the relevant terrain from that database. Second, the system may receive data input directly by users to indicate the nature of the terrain. Those inputs may be used to populate a geographical database or may be used to moderate the estimate of energy/effort for a particular activity. Thus, whilst engaged in an activity the user could designate by means of a user interface on a datalogger he is carrying the nature of the terrain over which he is passing. Third, the system may automatically estimate the nature of the terrain based on data sensed by the datalogger. For example, the datalogger could include one or more accelerometers and/or gyroscopes and the system could estimate the nature of relevant terrain in dependence on the data captured by those accelerometers and/or gyroscopes as a user crosses that terrain. In one example, increased variability of vertical and/or lateral acceleration derived from a linear accelerometer or of orientation information (e.g. absolute orientation or angular velocity) derived from a gyroscope could be taken to be representative of rougher terrain and therefore increased effort per unit time and/or distance. In another example, an increase in harmonics of the vertical and/or lateral acceleration and/or of such orientation information, or of their rates of change, above a predetermined frequency threshold could be taken to be representative of rougher terrain and therefore increased effort per unit time and/or distance. That threshold could, for example be in the range of 3 to 10 Hertz, or 5 to 10 Hertz.

Other sensors carried by the datalogger could also contribute to the estimation of the effort expended by the user. For example, the datalogger could sense one or more physiological characteristics of the user, such as pulse rate and respiration rate, and could use those, optionally in combination with pre-stored information relating to the user's physical characteristics such as resting pulse, pulse recovery rate, weight and VO2 max, to form an instantaneous estimate of the user's level of effort or exertion. That estimate can be summed or integrated over time to form an estimate of the total effort expended by a user in a particular session. Sensed data of that type may also be used to estimate the terrain. For example, the system may compare the user's current speed and/or gradient (e.g. as measured by a satellite positioning receiver integrated with the datalogger) and the current estimated effort of the user with previous contemporaneous pairings of current speed and estimated effort. A relatively high estimated effort in comparison to the current speed may be taken to indicate that the user is on more difficult terrain, and vice versa. Since effort may also be dependent on the gradient encountered by the user, the comparison may also take account of the user's current gradient, e.g. as determined from altitude measurements made by a satellite positioning receiver and/or a barometer integrated with the datalogger.

A further source of data to estimate effort is information received by the system that indicates the current environmental conditions, for example temperature, wind speed relative to the motion of a user and, for aquatic activities, water flow rate relative to the motion of a user. These could be determined from publically available information, e.g. using the internet, or from sensors installed specifically for the purpose of providing the effort-related data and that are capable of communicating with the device carried by a user.

The activity to be carried out on a route may be a compound activity made up of two or more individual forms of activity. One example is triathlon, which is made up of swimming, cycling and running. Another example is a run interspersed with static exercises such as press-ups. If the routes are to be used for a compound activity then another way to vary the routes so that they are comparable is to alter the split between the activities on the route. For example, the routes presented to each user could both follow flat 10 km pathways on straight roads, but to accommodate the fact that the temperature in the location of the first route is materially warmer than in the location of the second route, or that the first user is estimated to be less fit than the second user, the server could signal the first user's device to indicate that the first user is to cycle 5 km and run 5 km, whereas the server could signal the second user's device to indicate that the second user is to cycle 3 km and run 7 km. In general, the server could indicate to users' devices that the individual forms of activity that the respective users are to carry out in completing a route are different in number, length or duration with a view to the server making the routes comparable. In addition, it would be possible to specify entirely different forms of activity for each user (for example, one could run and the other could cycle) but where the level of effort or energy required of each user to complete each route by the method specified is equivalent.

Each route can comprise a start point, an end point and a path defined from the start point to the end point. A path in this context may comprise roads, dirt tracks, cycle paths, walkways, paths chosen by each user in open terrain, rivers, etc. each of which may be represented in the geographical database(s). The path uniquely defines a set of vectors that can be completed in order to go from the start point to the end point. The start point and/or the end point could be defined as distinct data sets, or implicitly by virtue of being the first and last points defined by the path.

In the manner described above, based on data that enables estimation of difficulty, the devices 10, 20 or server 30 can automatically select locations or routes in the vicinity of first and second selected user locations that have comparable levels of difficulty, and can provide those locations or routes to a pair of users. Each user can then time themselves to complete a respective one of the routes or activity in one of the locations, and the times can be compared. Since the routes or locations have been determined such that they are comparable, the users can have an expectation that their times for the routes or activities can fairly be compared. This allows those users to take part in a virtual race by competing along different routes and/or within different locations (or exercise/train together on different routes or in different locations) but in conditions that can be considered to be substantially equivalent. Either user may also specify certain parameters for the race or activity, such as preferred duration, preferred distance, preferred activity type, preferred terrain and preferred ascent, or a range of acceptable values for one or more of those parameters. The devices 10, 20 or server 30 will select comparable routes on the basis of those parameters. Alternatively, a user may select a certain kind of training goal, and the devices/server can select comparable routes based on available training programs or known performance-related information with a view to enabling the user to achieve his goal.

The system can also perform difficulty calculations and routing in real-time during a race or training session. For example, the device of each user can be capable of determining its location (potentially including altitude) during a race. Because a user's 2D location and altitude (and/or 3D location) can be known, other relevant factors such as the meteorological conditions, traffic conditions, change in elevation against a previous location, and the gradient of a slope on which the user is located can also all be determined. This real-time location and other information can be used to re-determine routes based on a current position such that the re-determined route still has the same difficulty as the original route. For example, if a user veers off the original route, the system can re-determine the route from the current position such that the remainder of the route has the same or similar difficulty as the remainder of the original route. In another example, if during a real-time race between a first and second user, the conditions for the first user changes such that the difficulty of the first user's route changes (e.g. adverse weather conditions, taking an alternative route, etc) then the server can determine the location of the second user and re-determine the second user's route from that location such that the difficulty of the re-determined route is comparable to the difficulty of the remaining route of the first user. The re-determined route can then be sent to the device of the second user. In appropriate situations, both routes can be adjusted.

In another example, one or more users may take part in training or in a race against others (or themselves) in real-time or at different times using historical data without the system determining any routes. One or more users may specify a target based on an amount of estimated effort to be exerted (e.g. time, distance, estimated amount of energy expended) and begin their activity (e.g. a run) on unknown and/or unspecified routes. A user's device can track the user's progress to calculate the effort exerted by the user in real-time. The calculated effort may be dependent on the data collected in real-time by the device (e.g. duration, location, altitude gain) which can be sent to the server. The server can use this and other data (e.g. meteorological conditions, traffic) to calculate the difficulty associated with the activity in progress by each user (e.g. similarly to the method described above but by determining the difficulty for the route completed thus far rather than the total route to be completed). The calculated difficulty can be used to estimate an amount of effort that has been exerted by the user. Because the difficulty of each route can be compared, the user devices or server can monitor and provide updates on each user's progress against the relevant target(s) and confirm when a race or activity has been completed.

Thus, in one example the system can pre-determine two geographically separate routes that are similar or normalized. The routes may be normalized by means of an algorithm that estimates the physical difficulty of the routes to a reference user, in which case the routes may be similar in that they are indicated by the algorithm as involving the same or closely similar physical difficulty to that user. Alternatively the routes may be normalized by means of an algorithm that estimates the physical difficulty of each route to the respective user, in which case the routes may be similar in that they are indicated by the algorithm as involving the same or closely similar physical difficulty to their respective users. The two routes can then be presented to the users so that the users can follow or "complete" the routes. The times taken by the users can then be compared, optionally together with other data about the users' physiological condition whilst completing the routes or shortly thereafter (e.g. pulse rate or pulse recovery time).

In another example two users can follow or complete two geographically separate routes and the system can determine a segment of each route that is normalized to a segment of the other route. The routes may be normalized by means of an algorithm that estimates the physical difficulty of the routes to a reference user, in which case the segments may be determined by identifying portions of each route that are indicated by the algorithm as involving the same or closely similar physical difficulty to that user. Alternatively the routes may be normalized by means of an algorithm that estimates the physical difficulty of segments of each route to the respective user, in which case the segments may be similar in that they are indicated by the algorithm as involving the same or closely similar physical difficulty to their respective users. The times taken by the users to complete the segments can then be compared, optionally together with other data about the users' physiological condition whilst completing the segments or shortly thereafter (e.g. pulse rate or pulse recovery time)

Figure 2:
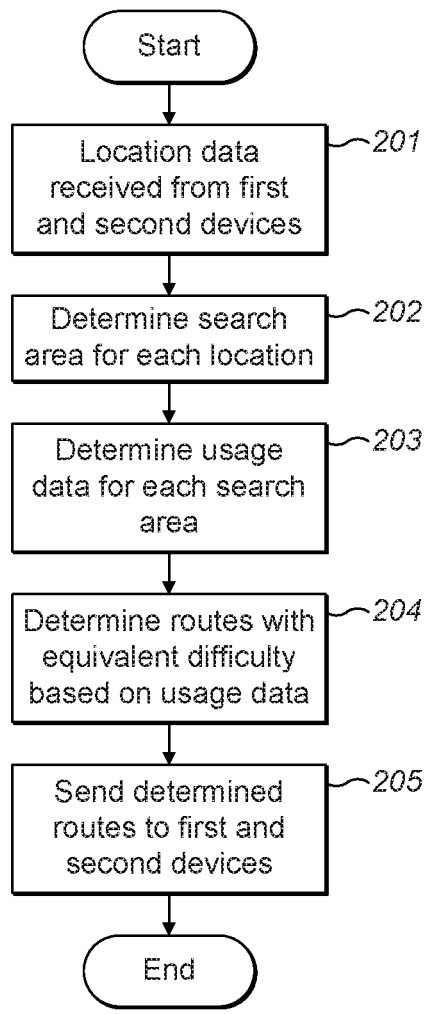
FIG. 2 depicts an example process for determining routes.
Figure 3:
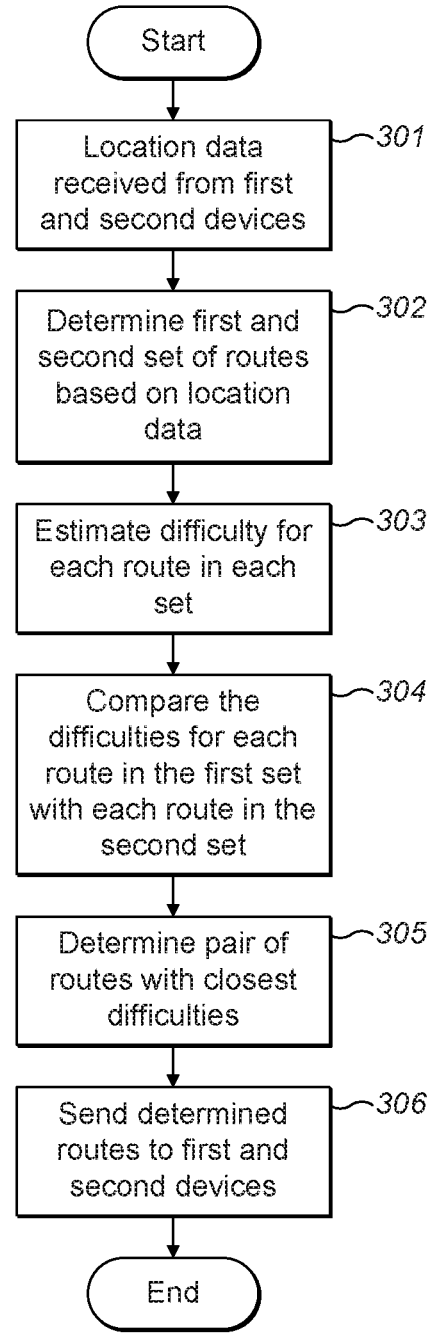
FIG. 3 depicts another example process for determining routes.
Figure 4:
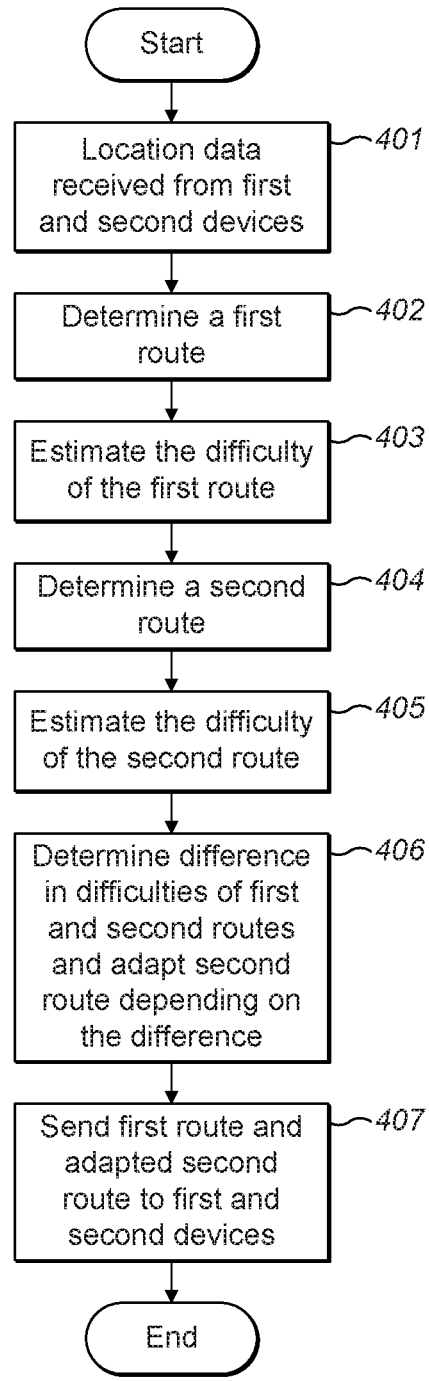
FIG. 4 depicts another example process for determining routes.

FIGS. 2 to 4 illustrate examples of how route information can be determined, normalized and provided to two different users in different locations.

FIG. 2 illustrates a first exemplary method for selecting two comparable routes in two different locations. At step 201, first location data is received from a first user and second location data is received from a second user. Also received from the first and/or second user can be at least one parameter for a race, such as the race duration. At step 202, the mapping services and/or geographic or other databases are analysed to determine a search area in the vicinity of each location. The size of the search area may be determined based on factors such as the specified duration, the activity, etc. For example, specifying a cycle race having a duration of 2 hours will lead to a larger area being searched than specifying a run for 15 minutes. At step 203, for each search area, data relating to the historical usage of routes in the area are determined. For example and as mentioned above, the usage data may indicate routes that have previously been used for physical activities such as running, cycling, etc. by the user or by other users. The data may indicate an average time taken for previous users to complete the routes. At step 204, based on the specified race duration, the historical usage data can be analysed to determine routes in each area that have average traversal times that are similar. As mentioned above, the average traversal time can be considered to indicate the physical difficulty of the route and thus two different routes with similar average traversal times can be considered to have equivalent physical difficulties. At step 205, the determined route in the search area of the first location is sent to the first user and the determined route in the search area of the second location is sent to the second user. A user may be able to accept or reject a proposed route; if a user rejects a route, the process described above would need to be repeated, until two comparable routes have been sent to, and accepted by, both users.

It may happen that the required number of routes cannot be identified as being comparable with a first identified route. For example, it might be impossible or undesirable to end a second route at a desired point because the end point would be in a tunnel where satellite positioning would be expected to be unavailable. In that case the start point of the second route could be adjusted to permit the second route to end at a suitable point and for the second route to be comparable to the first route. Alternatively, the first route could be adjusted (e.g. by being made longer or shorter). Thus in general the system could be arranged to identify that a route starts or ends at an undesirable location and in response to that identification to adjust the route by lengthening or shortening it so that it neither starts nor ends in an undesirable location. Undesirable locations may include: (a) locations where a device carried by a user might be expected to be unable to determine its location, such as locations that are indoors or underground, where the device would be shielded from satellite signals, (b) locations where it might be deemed inadvisable for a user to stop, such as in the middle of a highway and/or (c) locations that a user might not wish to stop, such as locations considered to be too far from where they wish to be at the end of the race, or those that might be considered unsafe, and so on.

FIG. 3 illustrates a second exemplary method for selecting two comparable routes in two different locations. At step 301, first location data is received from a first user and second location data is received from a second user. Also received from the first and/or second user is at least one parameter for the race, such as the race duration. At step 302, based on the first location data and the race duration, the mapping services and/or geographic or other databases are analysed to determine a first set of routes in the vicinity of the first location. Similarly, based on the second location data and the race duration, the mapping services and/or databases are analysed to determine a second set of routes in the vicinity of the second location. Each set may contain one or more determined routes. The length of the path for each route can be calculated based on the specified duration and, for example, an average speed of a cyclist (e.g. 15 mph) or the average speed logged by the user or other users on previous cycle rides. At step 303, the physical difficulty for completing each route in each set is estimated. For example, the mapping services and/or geographic or other databases can be analysed to calculate the total amount of incline along each path of each route. The total amount of incline can be used to estimate the difficulty of each route. At step 304, the difficulty estimates for each route in the first set is compared with the difficulty estimates for each route in the second set. At step 305, a pair of normalized routes with the closest matching difficulty estimates are determined to have equivalent or comparable difficulty. At step 306, the first route from the first set and the second route from the second set having equivalent difficulties are sent to the first and second users respectively. As before, a user may be able to accept or reject a proposed route; if a user rejects a route, the process described above would need to be repeated, until two comparable routes have been sent to, and accepted by, both users.

As before, if it is impossible or undesirable to end the second route at a desired point then the start point of the second route could be adjusted or the first route could be adjusted (e.g. by being made longer or shorter).

FIG. 4 illustrates a third exemplary method for selecting two comparable routes in two different locations. At step 401, first location data is received from a first user and second location data is received from a second user. Also received from the first and/or second user is at least one parameter for the race, such as the race duration. At step 402, based on the first location data and the race duration, the mapping services and/or geographic or other databases are analysed to determine a first initial route in the vicinity of the first location. The length of the path of the first initial route can be calculated in a manner similar to that described in step 302 above. At step 403, the physical difficulty of completing the first initial route is estimated. For example, the mapping services and/or geographic or other databases can be analysed to determine the total amount of incline along the path of first initial route. The incline data can be used to provide an estimate of the difficulty of the first initial route. At step 404, based on the second location data and the race duration, the mapping services and/or geographic or other databases are analysed to determine a second initial route in the vicinity of the second location. At step 405, the difficulty of the second initial route is estimated in a similar manner to that for the first initial route. If the estimated difficulties for the first and second initial routes are the same or within given acceptable parameters, the process moves on to step 407. At step 406, the second initial route is adapted so as to compensate for the difference in the estimated difficulties. For example, if the second initial route has a lower estimated difficulty, then the second initial route can be modified to have a longer path (e.g. by changing the path between the start and end points and/or moving the start and/or end points) to compensate for the difference. If the estimated difficulties for the two routes are very different (i.e. above some threshold difference in difficulty) then another second initial route may be chosen and adapted. Alternatively, the first initial route may be modified, or both routes may be modified. If there are no suitable unmodified or modified initial routes that are below the threshold difference in difficulty, then the process may move back to step 402, where another first initial route is determined. At step 407 the first initial route and the second initial route or adapted route(s) are sent to the first and second users respectively. As before, a user may be able to accept or reject a proposed route; if a user rejects a route, the process described above would need to be repeated, until two comparable routes have been sent to, and accepted by, both users.

In another embodiment two users could begin respective activities whilst each carrying a respective portable device that can identify their location and transmit and receive data to and from a communications network. Each device periodically transmits its location to a server that is also connected to the network. In real time the server makes an estimate of the difficulty endured by each user since they started the activity. The estimate of difficulty could be dependent on factors that include but are not limited to the speed of the respective user, the distance travelled by the respective user, terrain on the route traversed by the user as indicated to the server by a geographical database. The estimate of difficulty could optionally also be dependent on factors particular to the respective user such as their age, sex or physical fitness. The server provides to each user data indicating the difficulty endured by the user compared to the difficulty endured by the other user. This may be provided as a notional difficulty score (e.g. one user being 100 points behind the other), as a ratio (e.g. one user being 10% behind the other), as an estimate of energy expended (e.g. one user has expended 200 calories more than the other) or as a notional distance that one user is ahead of the other (e.g. "user A is 100 m ahead", representing the fact that the server has estimated that user B would need to have travelled an additional 100 m beyond where he is now in order to have endured the same difficulty as user A currently has). This data can be indicated to each user in order to allow them to gauge their performance against the other user. It may be indicated on a display, by audio or in another manner. It may be indicated directly as received from the server, or it may be translated by the device before presentation. Conveniently the users start their activities at the same time, but one user could start before the other, allowing the first user a head start; or the server could compare a user's performance against a recorded performance for the same or another user.

Each of the portable devices could be carried by a respective user. The devices could be in the form of a cellular telephone, watch or data logger, or a combination of these communicatively connected physically or wirelessly to each other. The device could comprise a memory storing in a non-transitory form software for causing the device to perform in the manner set out above. The software could be native to the device or could be an optional addition to it, for example in the form of an application. The server could comprise or have access to a memory storing in a non-transitory form software for causing the server to perform in the manner set out above.

The processes illustrated in the examples of FIGS. 2 to 4 can be utilised for more than two participants, each having a different location. In the examples above, the difficulty of a route is based on a single indicator such as total ascent of a route or average traversal time. However, other indicators, such as terrain, altitude, and meteorological conditions, or a combination of two or more indicators can be used to determine the difficulty of a route. Also, one or more race parameters (other than or as well as duration) can also be specified by the user(s) for determining the routes (e.g. specifying start and/or end points, path distance, preferred road types, etc).

The route information provided to the users enable them to race in different locations, while having confidence that the conditions for the competition have been normalized and are similar and fair. The users may choose to race in real-time or at different times and have their race progress logged and/or sent (in real-time or at some later time) to the other user for comparison.

The estimation of the difficulty of a route and determination of the equivalency in the difficulties of two routes can be increased in accuracy by, for example, segmenting each route into a plurality of segments. For example, using the total incline (as described above) may not account for parts of the route that are very steep, which may be more difficult than a gradual incline. By segmenting the routes and estimating physical difficulties on a per segment basis, a more accurate difficulty estimation of the whole route can be determined. Comparing the segments of two routes can help to determine equivalent physical difficulties more accurately.

Furthermore, the segments of a route may be ordered (e.g. beginning, middle and end segments or by their specific distance from the start of the route) and compared with the segments of another route on the basis of the ordering. This can enable users to race on routes with comparable difficulties at similar stages in the race. Some variables used in calculating the difficulty, (e.g. inclination, terrain, etc) can be weighted differently depending on where they appear in the race. For example, three steep hills at the beginning segment of a race can impact on the difficulty of the race differently than if the hills were at the end of the race. These weighted variables can be used to determine the difficulty of the whole route and/or segments of the route.

In the examples described above the routes are determined as being comparable in the sense that the data available to the device(s) calculating the routes indicates that the same user would be expected to expend the same level of effort and/or take the same time to complete each route. This means that the users can race over the routes and achieve a result that mimics the result of them racing each other over the same course. In an alternative embodiment, the routes are also selected in dependence on one or more characteristics of the users, and are comparable in the sense that the data available to the device(s) calculating the routes indicates that each user would be expected to take the same time to complete his route as the other user(s) would be expected to take to complete their route(s). To achieve this the estimation of the time taken to complete each route may be modified based on available data relating to the user to whom the route is to be presented. Examples of how this might be done are as follows:

1. The estimated effort and/or time may be adjusted by predetermined factors for available information about the user such as age, sex, home altitude, physical condition or ability, ranking in national, local or other leagues relevant to the specified activity, time since last exercise, average pace completing routes over the past month, weight and resting pulse rate. For instance, the estimated time may be multiplied by 1.2 if the user is aged between 55 and 60, or by 1.3 if the user is a habitual smoker or by 1.4 if the user's weight is between 90 and 100 kgs.

2. When the effort and/or time estimate is based on data from other users' past results, the system could select only a subset of the available users' data to provide the basis for the computation, that subset being a group of users whose attributes match those of the user to whom the route is to be presented.

The system described herein is particularly beneficial for permitting users who are distant from one another to compete. Hence, in some circumstances the routes may be selected such that they do not cross each other, or do not overlap each other, or approach each other no more closely than a distance such as 10 or 20 km. Indeed, two or more users may, for example, compete or participate in joint activities with each other while in different regions, countries or continents.

Once a route has been provided to a user's device, the device may display to the user a map on which the route is superimposed. Further, once the route has been accepted, the display could show markers on the route to indicate where the user or other users who have run or are running on the same or different routes are or would be placed on the route, either at a particular point during the activity or in real time. The device may be used as a stopwatch to log the time taken by the user to complete the route and, if the device is able to determine its location, to indicate the user's progress (e.g. via a display or via audio through speakers or headphones connected to the device) along the route and log his time over sub-parts of the route. Once the user has completed the route the device may upload the user's time to complete the route to the server 30 or to another server so that the results of the competition can be compared online. In recording the user's time the device may automatically pause when the user encounters an obstacle such as traffic, or a road crossing that could, for example, be detected through the user pausing at a road junction or at a location where the route crosses a road.

The device may be able indicate the user's progress during a race or training session as well as the user's progress relative to one or more other users. For example, the device of each user can periodically send its location to the server, which can then use that data to calculate each user's progress during a race. The server can then periodically send each user indications of the progress of the other users (e.g. the progress indicator could be a calculated percentage of the route completed, the calculation can be dependent on factors such as current location, route difficulty, total distance and elapsed race time). Thus the race progress of each competitor can be tracked in real-time. The user may also track his progress against saved historical progress data (e.g. when competing against other users who have already completed their route or against the user's own historical race/training data).

In examples described above the following of routes generated by the system has been described as being a race. The routes could be followed for non-competitive recreational purposes, including training, or for competitive purposes.

In some of the examples described above the system generates specific routes for users. In another embodiment the system may identify comparable areas (e.g. parks or lakes) within which users in different locations can complete a particular activity. The activity may be predefined by one or both of the users or may be selected by the system from a predetermined set of activities. The activity may, for example be running a mile or swimming 500 m. The system can then provide each identified area to a respective one of the users. Each user may then undertake the activity in a respective one of the areas.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A method of providing route information to a plurality of users by means of a data processing device, the method comprising:
   receiving a first location and a second location;
   analysing one or more databases selected from the group comprising mapping services, geographic databases and other databases and thereby determining a pair of routes, each route comprising a start point, an end point and a defined path from the start point to the end point, the step of analysing comprising determining the routes such that (a) a first one of the routes is in the vicinity of the first location and a second one of the routes is in the vicinity of the second location and (b) the routes are of comparable difficulty for the users to complete; and
   providing the first route to a first one of the users and providing the second route to a second one of the users.

2. A method as claimed in claim 1, wherein the step of analysing comprises estimating the physical difficulty of each route and determining that the estimated physical difficulty of the routes are within a predetermined threshold of each other.

3. A method as claimed in claim 2, wherein the physical difficulty of a route is represented as an estimated level of effort or time to complete that route.

4. A method as claimed in claim 1, wherein the step of analysing comprises estimating the physical difficulty of each route and estimating based on data defining one or more personal characteristics of the users that the first one of the users will take a time to complete the first route that is within a predetermined threshold of a time that the second one of the users will take to complete the second route.

5. A method as claimed in claim 4, wherein the personal characteristic(s) comprise one or more of the following characteristics: sex, weight, resting pulse, VO2 max, maximum heart rate, physical condition, physical ability, home altitude and age.

6. A method as claimed in claim 1, wherein the step of determining that the routes are of comparable difficulty for the users to complete comprises estimating the physical difficulty of each route by summing weighted estimates of one or more characteristics of that route.

7. A method as claimed in claim 6, wherein the characteristics of the route comprise one or more of distance, ascent, altitude and a value representing terrain.

8. A method as claimed in claim 1, wherein the step of determining that the routes are of comparable difficulty for the users to complete comprises estimating the physical difficulty of each route by means of data gathered from them and/or other users who have previously completed the routes or parts of them and/or devices employed along the specified routes.

9. A method as claimed in claim 1, wherein the step of determining that the routes are of comparable difficulty for the users to complete comprises estimating the physical difficulty of each route by averaging one or more performance metrics gathered from other users in completing the routes or parts of them.

10. A method as claimed in claim 9, wherein the performance metrics include one or more of: average effort and/or time among a group of other users to complete the route or part of it, average speed among a group of other users in completing the route or part of it and average cadence among a group of other users in completing the route or part of it.

11. A method as claimed in claim 1, wherein the step of analysing comprises determining the routes to be comparable by the steps of:
   determining a first candidate route;
   determining a second candidate route;
   comparing the candidate routes and if they are not the same or within acceptable levels of similarity; subsequently
   determining a sub-part of one of the first and second candidate routes that is comparable to the other of the first and second candidate routes; and
   selecting the sub-part of one of the first and second candidate routes as the first route and selecting the other of the first and second candidate routes as the second route.

12. A method as claimed in claim 1, wherein the step of analysing comprises determining the routes to be comparable by the steps of:
   determining a first candidate route;
   determining a second candidate route;
   comparing the candidate routes and if they are not the same or within an acceptable level of similarity; subsequently
   modifying either or both of the first and second candidate routes so that they are the same or within an acceptable level of similarity; and
   selecting the candidate routes after appropriate modification to either or both of them.

13. A method as claimed in claim 1, wherein the step of analysing comprises determining the routes to be comparable by the steps of:
   determining a first candidate route;
   determining a second candidate route;
   comparing the candidate routes and if they are not the same or within an acceptable level of similarity; subsequently
   modifying either or both of the first and second candidate routes so that they are the same or within an acceptable level of similarity; and
   selecting the candidate routes after appropriate modification to either or both of them;
   wherein the step of modifying involves processes aimed not simply at identifying comparable routes in terms of difficulty but comparable routes optimised for greatest convenience, safety or other benefits for or goals specified by users.

14. A method as claimed in claim 1, comprising the steps of:
   the first user completing the first route; and
   the second user completing the second route.

15. A method as claimed in claim 14, wherein during the said steps of completing the routes the first user and the second user travel on at least parts of their respective routes simultaneously.

16. A method as claimed in claim 14, wherein during the said steps of completing the routes the first user and the second user start travelling on their respective routes simultaneously.

17. A method as claimed in claim 14, wherein the first user completes the first route before the second user starts travelling on the second route.

18. A method of providing performance information to a first user, the method comprising:
estimating, using a first transceiver device local to the first user, first user location data comprising a location of the first user at each time in a first series of times;
transmitting from the first transceiver device to a data processing device remote from the first user, the first user location data;
estimating at the data processing device, in dependence on the location data, a difficulty of a first route traversed by the first user during the first series of times;
comparing the difficulty of the first route with a difficulty of a second route traversed by a second user and thereby forming result data representing the result of that comparison;
transmitting the result data from the data processing device to the first transceiver device; and
presenting the result data to the first user by means of the first transceiver device local to the first user.

19. A method as claimed in claim 18, wherein the method comprises:
estimating, using a second transceiver device local to a second user, second user location data comprising a location of the second user at each time in a second series of times;
transmitting from the second transceiver device to the data processing device the second user location data;
estimating at the data processing device, in dependence on the second location data, the difficulty of the second route; and
wherein the step of comparing comprises comparing the estimated difficulty of the first route with the estimated difficulty of the second route.

20. A method as claimed in claim 18, wherein the step of comparing comprises comparing the estimated difficulty of the first route with pre-stored data representing the estimated difficulty of the second route traversed by the second user.

21. A method as claimed in claim 1, wherein each route comprises at least one of a driving route and a cycling route.

22. A method as claimed in claim 1, wherein each route comprises at least one of a sailing route, a kayaking route, and a skiing route.

23. A method as claimed in claim 1, wherein each route comprises a vehicle route.

24. A method as claimed in claim 1, wherein analysing comprises using topographical information from a geographic database to determine the routes such that the routes are of comparable difficulty for the users to complete.

25. A method as claimed in claim 18, wherein the first route and the second route comprises at least one of a driving route and a cycling route.

26. A method as claimed in claim 18, wherein the first route and the second route comprises at least one of a sailing route, a kayaking route, and a skiing route.

27. A method as claimed in claim 18, wherein the first route and the second route comprise a vehicle route.

28. A method as claimed in claim 19, wherein the first series of times and the second series of times are the same times.

29. A method of providing route information to a data processing device user, the method comprising:
estimating difficulty of a route using data automatically logged by a data logger device comprising at least one of an accelerometer and a gyroscope, the data comprising at least one of acceleration data and orientation data obtained while a data logger device user traverses the route with the datalogger device; and
proving a resulting estimate of difficulty of the route to a data processing device used by the data processing device user.

30. A method as claimed in claim 29, wherein the data comprises acceleration data and a variability in acceleration over a time duration of traversing the route is used to estimate difficulty of the route.

31. A method as claimed in claim 29, wherein the data comprises orientation data and changes in orientation over time while traversing the route is used to estimate difficulty of the route.

32. A method as claimed in claim 29 wherein estimating difficulty of a route further comprises using data from a physiological sensor related to user exertion and obtained while the data logger device user traverses the route with the physiological sensor.

33. A method as claimed in claim 32 wherein the data from the physiological sensor comprises one or more of a pulse rate and a respiration rate.

34. A method as claimed in claim 32 wherein estimating difficulty of a route further comprises using the data from the physiological sensor in combination with pre-stored information relating to the data logger device user's characteristics comprising at least one of resting pulse, pulse recovery rate, weight, VO2 max, age, sex, and physical condition.

35. A method as claimed in claim 32 wherein estimating difficulty of a route further comprises using the data from the physiological sensor in combination with data reflecting the data logger user's exertion on one or more other routes.

* * * * *